(12) United States Patent
Williams et al.

(10) Patent No.: US 10,653,398 B2
(45) Date of Patent: May 19, 2020

(54) ADAPTER ASSEMBLIES FOR SURGICAL DEVICES

(71) Applicant: Covidien LP, Mansfield, MA (US)

(72) Inventors: Justin Williams, Southbury, CT (US); Stephen Paul, East Hartford, CT (US)

(73) Assignee: Covidien LP, Mansfield, MA (US)

( * ) Notice: Subject to any disclaimer, the term of this patent is extended or adjusted under 35 U.S.C. 154(b) by 810 days.

(21) Appl. No.: 15/229,220

(22) Filed: Aug. 5, 2016

(65) Prior Publication Data

US 2018/0035987 A1   Feb. 8, 2018

(51) Int. Cl.
*A61B 17/00* (2006.01)
*A61B 17/115* (2006.01)
(Continued)

(52) U.S. Cl.
CPC ........ *A61B 17/00* (2013.01); *A61B 17/00234* (2013.01); *A61B 17/1155* (2013.01);
(Continued)

(58) Field of Classification Search
CPC .............. A61B 17/00; A61B 17/00234; A61B 2017/00353; A61B 2017/00367; A61B 2017/00371; A61B 2017/00389; A61B 2017/00398; A61B 2017/00411; A61B 2017/0046; A61B 2017/00464; A61B 2017/00473; A61B 2017/00477;
(Continued)

(56) References Cited

U.S. PATENT DOCUMENTS 2,777,340 A   1/1957   Hettwer et al.
2,957,353 A   10/1960   Babacz
(Continued)

FOREIGN PATENT DOCUMENTS

CA   2451558 A1   1/2003
CN   1547454 A   11/2004
(Continued)

OTHER PUBLICATIONS

Partial European Search Report dated Dec. 22, 2017, issued in EP Application No. 17184857.
(Continued)

*Primary Examiner* — Ahmed M Farah
(74) *Attorney, Agent, or Firm* — Carter, DeLuca & Farrell LLP

(57) ABSTRACT

An adapter assembly includes a base member, a housing, and a locking mechanism. The base member defines a longitudinal axis. The housing is rotatably secured to the base member and is rotatable in relation to the base member between a plurality of positions. The locking mechanism is supported on the housing and includes a locking member and a button. The locking member is moveable from a locked position in which a lock of the locking member is engaged with the base member to secure the housing in one of the plurality of positions to an unlocked position in which the housing is rotatable in relation to the base member. The button is positioned on the base member and is depressible to translate the locking member in a direction parallel to the longitudinal axis from the locked position to the unlocked position.

7 Claims, 12 Drawing Sheets

(51) Int. Cl.
*A61B 34/30* (2016.01)
*A61B 17/072* (2006.01)

(52) U.S. Cl.
CPC ...... *A61B 34/30* (2016.02); *A61B 2017/0046* (2013.01); *A61B 2017/00398* (2013.01); *A61B 2017/00473* (2013.01); *A61B 2017/00486* (2013.01); *A61B 2017/07221* (2013.01)

(58) Field of Classification Search
CPC ......... A61B 2017/00486; A61B 2017/007214; A61B 2017/007221
USPC ............................ 606/1, 130, 167, 205, 219
See application file for complete search history.

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,514,157 A * | 5/1996 | Nicholas ............ A61B 17/0218 600/201 |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |

(56) References Cited

U.S. PATENT DOCUMENTS

| | | |
|---|---|---|
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,052,636 B2 * | 11/2011 | Moll ............... A61B 34/71 604/95.04 |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,679,098 B2 * | 3/2014 | Hart ............... A61B 17/29 604/22 |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,789,737 B2 | 7/2014 | Hodgkinson et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Iveisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |

(56) References Cited

U.S. PATENT DOCUMENTS

| | | |
|---|---|---|
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,629,633 B2 * | 4/2017 | Williams ............. A61B 17/115 |
| 10,485,549 B2 * | 11/2019 | Williams ........... A61B 17/3205 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0184946 A1 * | 7/2012 | Price .............. A61B 17/320092 606/1 |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |

(56) References Cited

U.S. PATENT DOCUMENTS

| | | |
|---|---|---|
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 1957854 A | 5/2007 |
| CN | 101495046 A | 7/2009 |
| CN | 102247182 A | 11/2011 |
| DE | 102008053842 A1 | 5/2010 |
| EP | 0705571 A1 | 4/1996 |
| EP | 1563793 A1 | 8/2005 |
| EP | 1769754 A1 | 4/2007 |
| EP | 2316345 A1 | 5/2011 |
| EP | 2668910 A2 | 12/2013 |
| EP | 3123960 A1 | 2/2017 |
| ES | 2333509 A1 | 2/2010 |
| JP | 2005-125075 A | 5/2005 |
| KR | 20120022521 A | 3/2012 |
| WO | 2011/108840 A2 | 9/2011 |
| WO | 2012/040984 A1 | 4/2012 |

OTHER PUBLICATIONS

Extended European Search Report corresponding to counterpart International Application No. EP 14 18 4882.0 dated May 12, 2015.
Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. Ep 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended 2016 European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
U.S. Appl. No. 14/875,766, filed Oct. 6, 2015.

* cited by examiner

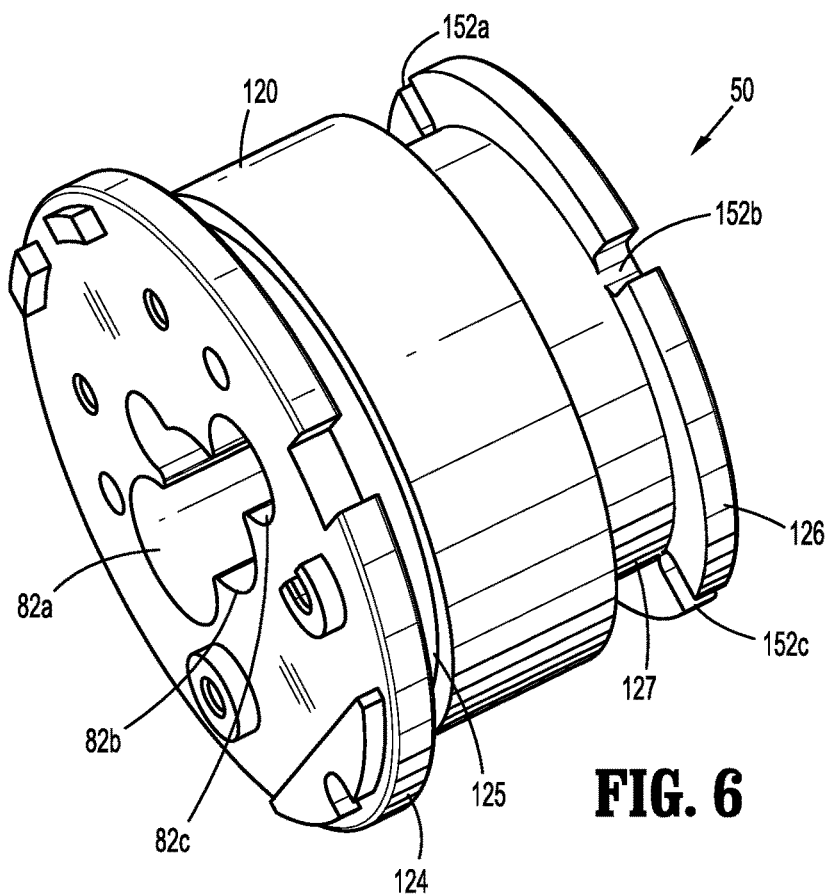
FIG. 6
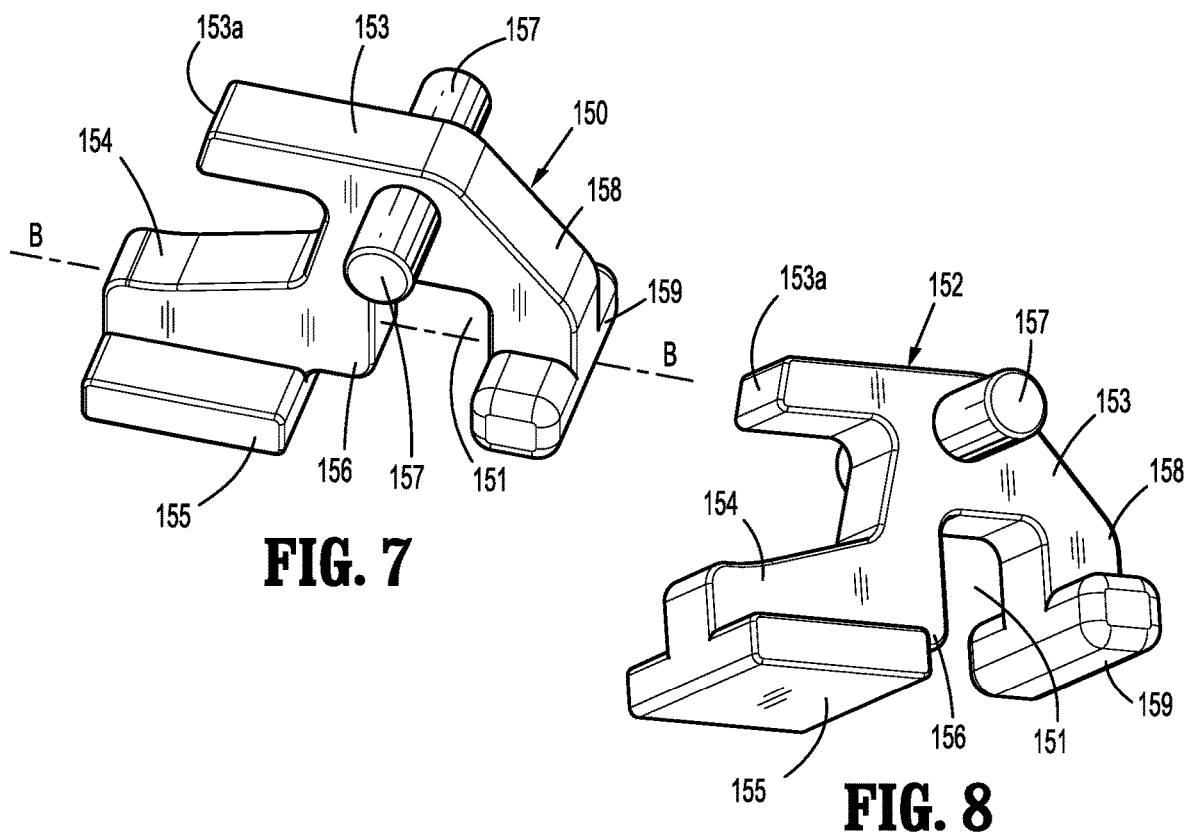
FIG. 7
FIG. 8

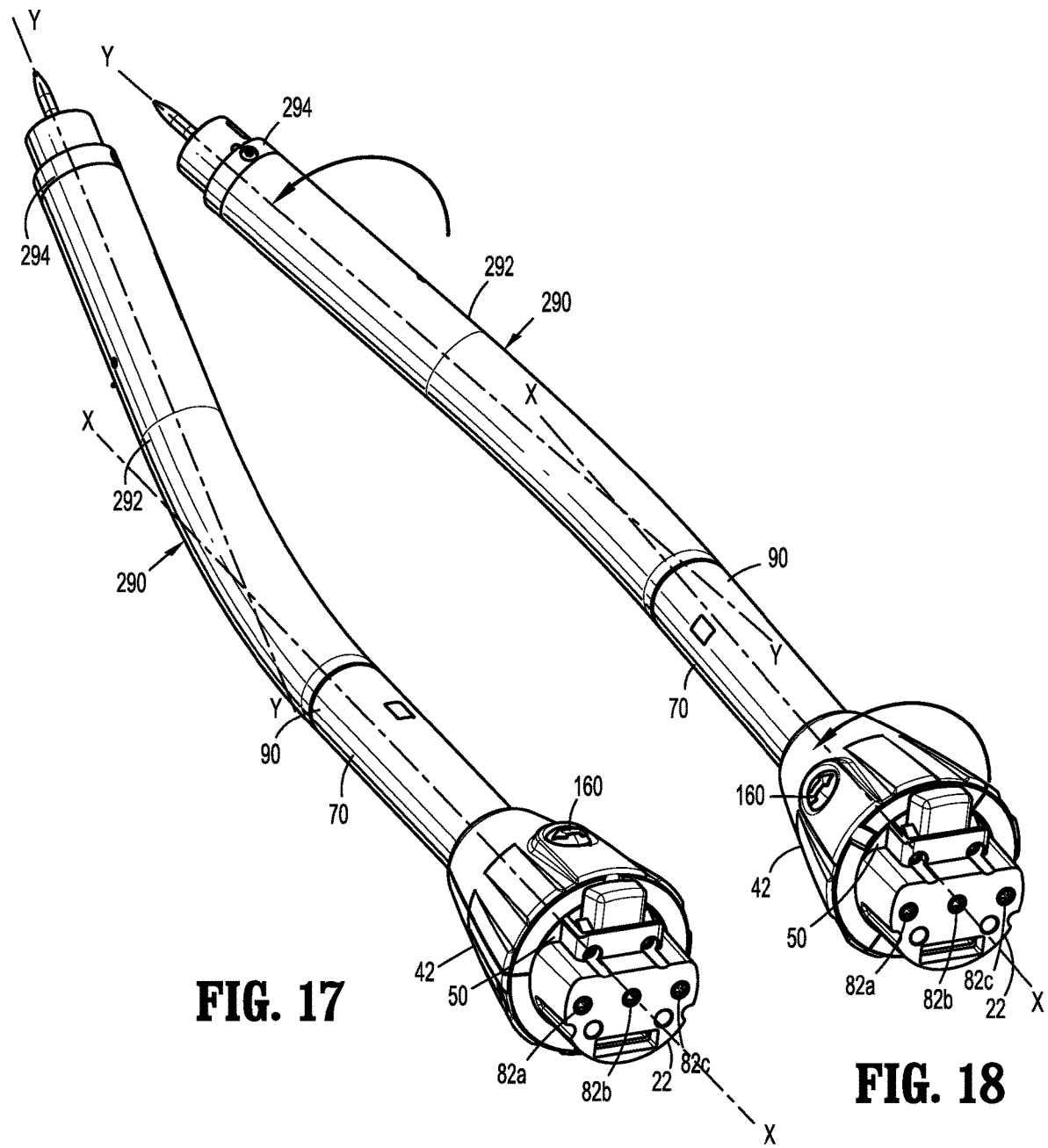

ADAPTER ASSEMBLIES FOR SURGICAL DEVICES

BACKGROUND

1. Technical Field

The present disclosure relates generally to adapter assemblies for selectively connecting end effectors to actuation units of surgical devices. More specifically, the present disclosure relates to adapter assemblies having a locking mechanism for rotationally securing a housing to a base.

2. Background of Related Art

Powered devices for use in surgical procedures typically convert rotational motion from an actuation assembly to linear motion for effectuating one or more functions, e.g., clamping, stapling, cutting. To permit rotational alignment of an end effector attached to the actuation assembly without the operator having to manipulate the actuation assembly in an uncomfortable or awkward position, adapter assemblies have been developed for enabling selective rotation of the end effector relative to the actuation assembly. Such adapter assemblies generally include a base that is fixedly secured to the actuation assembly and a body to which an end effector is attached that is rotatable relative to the base and the actuation assembly.

It would be beneficial to provide a surgical device including an adapter assembly with a locking mechanism that facilitates selective rotation of the body relative to the base but resists rotating forces that a clinician may exert on the body during use to prevent inadvertent rotation of the body relative to the base.

SUMMARY

This disclosure relates generally to adapter assemblies including a base member, a housing, and a locking mechanism for selectively securing the housing in a plurality of radial positions relative to the base member. The base member is securable to an actuation handle for actuating a tool assembly supported by the adapter assembly. The rotation of the housing affects the position of the end effector relative to the actuation handle.

In an aspect of the present disclosure, an adapter assembly includes a base member, a housing, and a locking mechanism. The base member defines a longitudinal axis of the adapter assembly. The housing is rotatably secured to the base member and is rotatable in relation to the base member between a plurality of positions. The locking mechanism is supported on the housing and includes a locking member and a button. The locking member is moveable from a locked position in which a lock of the locking member is engaged with the base member to secure the housing in one of the plurality of positions to an unlocked position in which the housing is rotatable in relation to the base member. The button is positioned on the base member and is depressible to translate the locking member in a direction parallel to the longitudinal axis from the locked position to the unlocked position.

In aspects, the locking member has a boss and the button defines a cam slot that receives the boss. The button may have an undepressed position in which the boss is positioned adjacent a first end of the cam slot and a depressed position in which the boss is positioned adjacent a second end of the cam slot. Walls defining the cam slot can engage the boss as the button is moved towards the depressed position to translate the locking member in the direction parallel to the longitudinal axis as the boss moves towards the second end of the cam slot. The adapter assembly may include a biasing member disposed between the button and the locking member that urges the button towards the undepressed position.

In some aspects, the base member includes an annular flange that defines first and second cutouts. The locking member may have a lock body, a distal leg, and a proximal leg. The distal and proximal legs may define a gap therebetween. In the unlocked position of the locking member, the annular flange may be rotatable within the gap. The lock of the locking member may extend proximally from the distal leg and be disposable within one of the first or second cutouts to secure the housing in one of the plurality of positions. The annular flange may define a third cutout that is diametrically opposed to the first cutout with the second cutout positioned between the first and third cutouts. The second cutout may be equidistant from the first and third cutouts.

In certain aspects, the housing defines a channel and the button is disposed within the channel.

In particular aspects, the adapter assembly includes a coupling body that extends from the housing and is rotatably fixed to the housing. The coupling body may have a proximal portion that includes a tab. The housing may define a recess that receives the tab to rotatably fix the coupling body to the housing.

In another aspect of the present disclosure, a surgical device includes a handle, a tool assembly, and an adapter assembly. The adapter assembly interconnects the handle and the tool assembly. The adapter assembly includes a base member, a housing, and a locking mechanism. The base member defines a longitudinal axis and the housing is rotatably secured to the base member. The housing is rotatable in relation to the base member between a plurality of positions such that rotation of the housing affects a position of the tool assembly relative to the handle. The locking mechanism is supported on the housing and includes a locking member and a button. In a locked position of the locking member, a lock of the locking member is engaged with the base member to secure the housing in one of the plurality of positions. In an unlocked position the housing is rotatable in relation to the base member. The button is positioned on the base member and is depressible to translate the locking member in a direction parallel to the longitudinal axis from the locked position to the unlocked position.

In aspects, the surgical device includes an extension assembly that includes a shaft having first and second ends. The first end of the shaft may be releasably coupled to a distal end of the adapter assembly and the second end of the shaft may support the tool assembly. The shaft may be curved between the first and second ends.

In some aspects, the adapter assembly includes a coupling body that extends from the base member. The coupling body may be rotatably fixed to the housing.

In certain aspects, the adapter assembly includes a coupling assembly that extends proximally from the base member and is releasably secured to the handle. The adapter assembly may include a drive assembly that extends through the coupling assembly, the base member, and the housing. The handle may engage the drive assembly to actuate the tool assembly. The drive assembly may include first and second connectors that are disposed within the coupling assembly. The first connector may be offset form the longitudinal axis.

In another aspect of the present disclosure, a method of reposition a tool assembly supported by an adapter is disclosed. The adapter defines a longitudinal axis and is coupled to a handle that is configured to actuate the tool assembly. The method includes depressing a button of the adapter, rotating the handle relative to the housing, and releasing the button. Depressing the button translates a locking member in a direction parallel to the longitudinal axis from a locked position, in which the handle is rotatably fixed relative to a housing of the adapter in a first position, to an unlocked position. Rotating the handle relative to the housing includes rotating a base member of the adapter within the housing with the locking member in the unlocked position such that the tool assembly is repositioned about relative to the handle. Releasing the button allows the locking member to return to the locked position with the housing rotatably fixed to the handle in a second position different from the first position.

In aspects, depressing the button of the adapter includes walls defining a cam slot of the button engaging a boss of the locking member to translate the locking member towards the unlocked position.

In some aspects, the method includes rotating the handle to the second position after releasing the button. Rotating the handle to the second position may include the locking member transitioning to the locked position when the handle reaches the second position. The locking member may provide feedback with the handle reaches the second position.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 6 is a side, perspective view from the proximal end of the base member of FIG. 4;

FIG. 7 is a top perspective view of a locking member of the locking mechanism of FIG. 4;

FIG. 8 is a bottom perspective view of the locking member of the locking mechanism of FIG. 4;

FIG. 17 is a perspective view of the base member and the body of the adapter assembly shown in FIG. 1 in a first radial position relative to one another; and FIG. 18 is a perspective view of the base member and the body of the adapter assembly shown in FIG. 17 in a second radial position relative to one another.

DETAILED DESCRIPTION OF EMBODIMENTS

Figure 1:
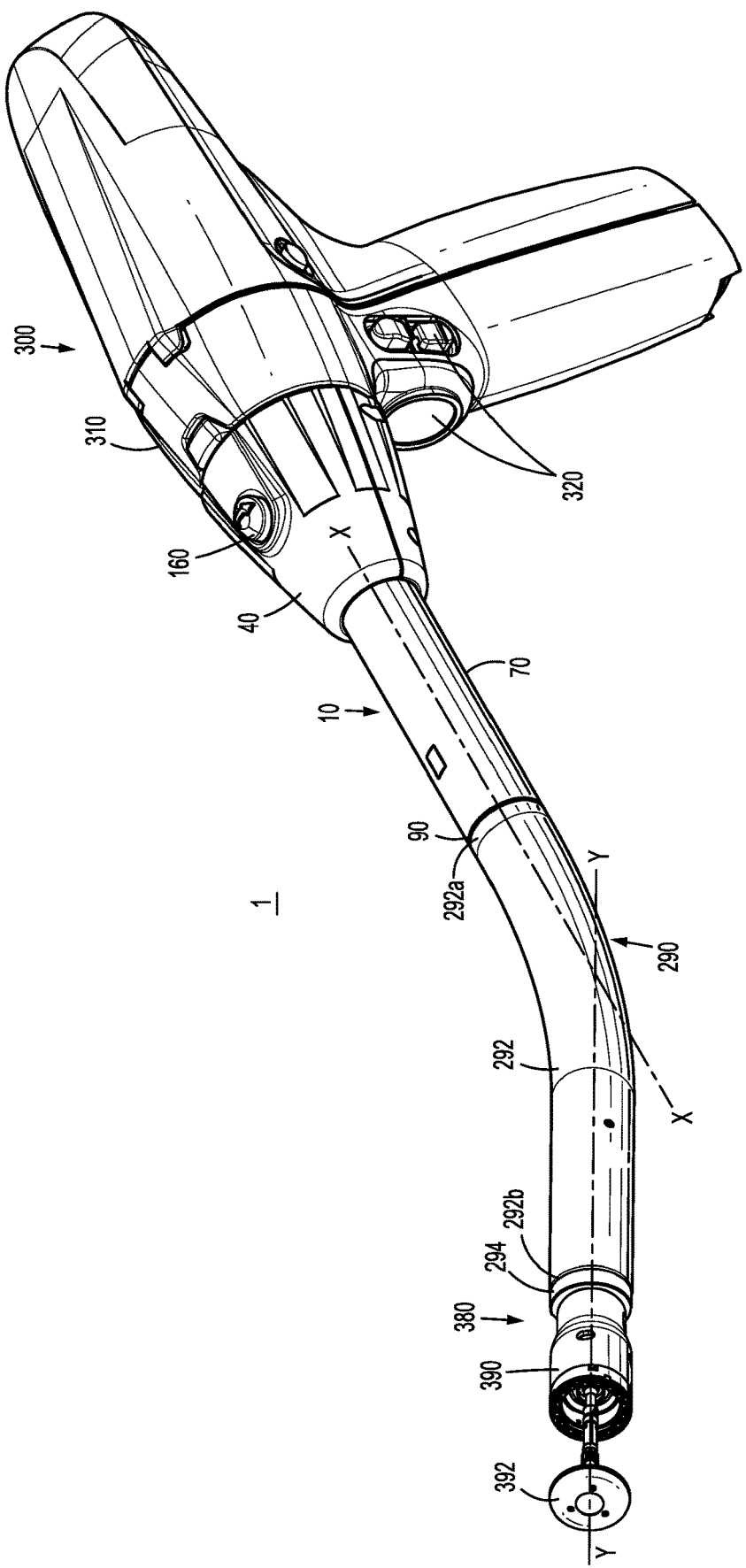
FIG. 1 is a side, perspective view of a surgical device including an exemplary embodiment of an adapter assembly provided in accordance with the present disclosure.

This disclosure relates generally to adapter assemblies that include a base member, a housing, and a locking mechanism for selectively securing the housing in a plurality of radial positions about the base member. The base member can be selectively coupled to an actuation assembly such that the base member is rotatably fixed to the actuation assembly. The housing is rotatable about the base member such that a tool assembly supported by the housing of the adapter assembly is repositionable relative to the actuation assembly. The locking mechanism is provided to selectively lock the orientation of the housing relative to the base member and includes a locking member and a button. In embodiments, the locking member is slidable in a direction parallel to a longitudinal axis defined by the adapter assembly between a locked position and an unlocked position. The button may define a cam slot that receives a boss of the locking member such that walls defining the cam slot engage the boss to translate the locking member between the locked and unlocked positions.

Embodiments of the presently disclosed adapter assembly are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Figure 2:
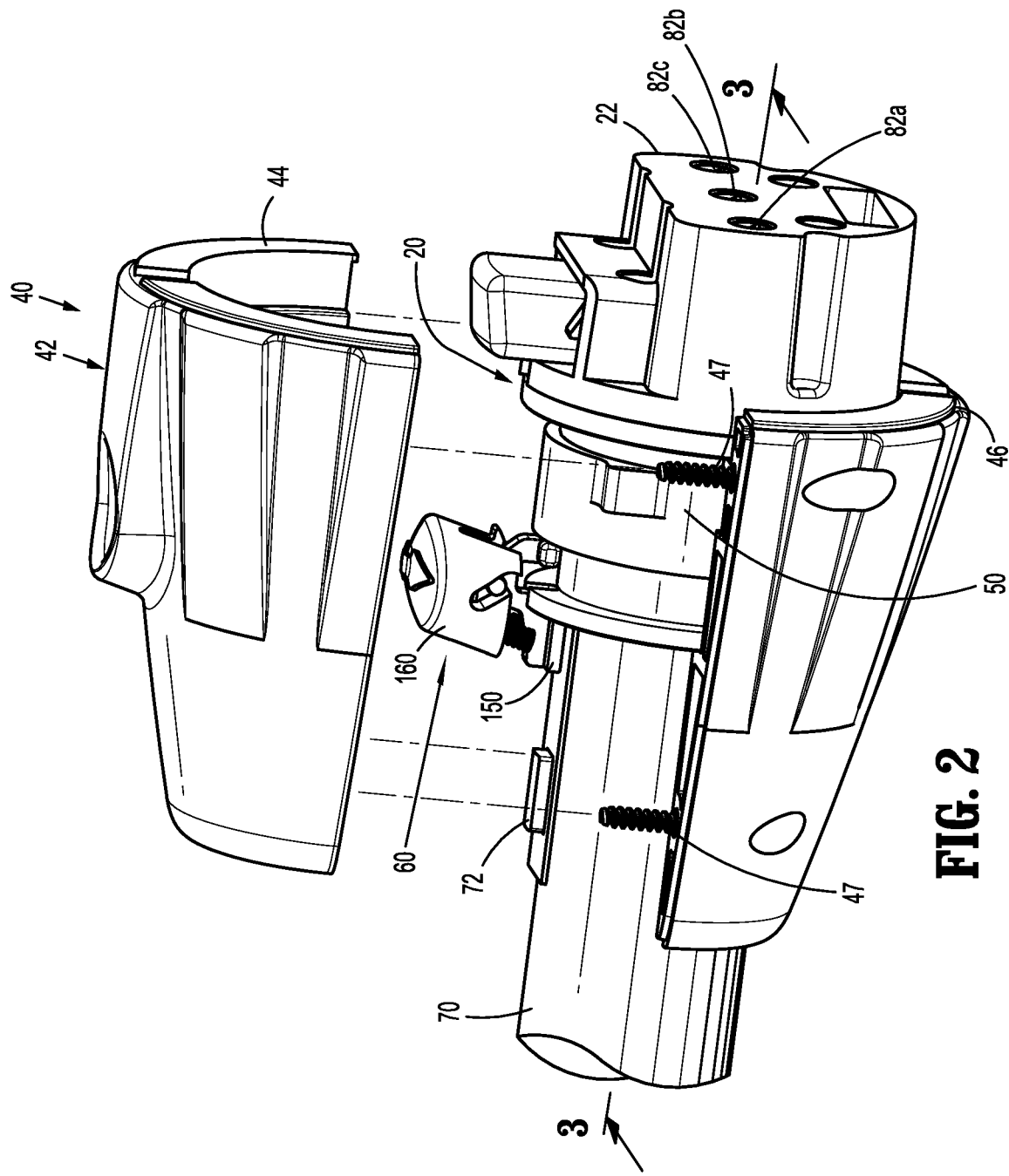
FIG. 2 is an enlarged, perspective, cutaway view of a proximal portion of the adapter assembly of FIG. 1.
Figure 15:
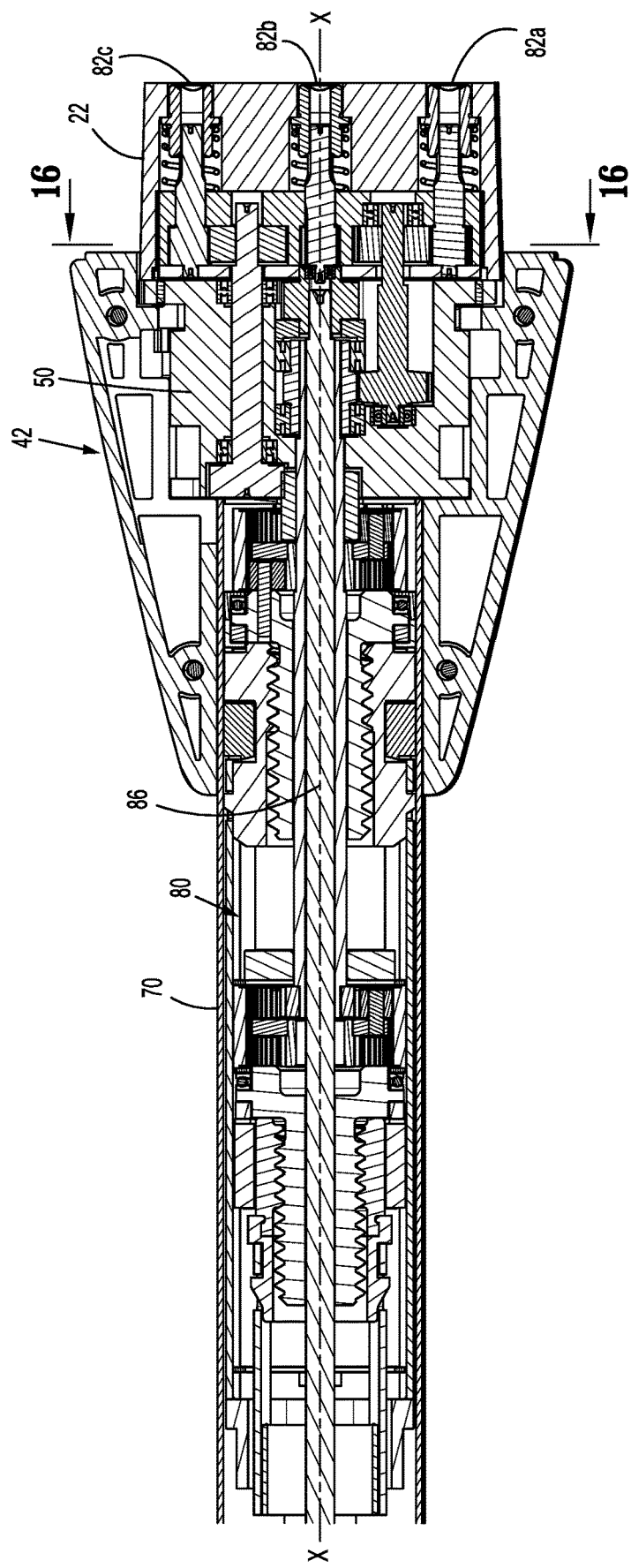
FIG. 15 is a cross-sectional view taken along section line 15-15 of FIG. 3.

Referring to FIGS. 1 and 2, a surgical device 1 including an exemplary adapter assembly 10 is provided in accordance with the present disclosure. As shown, the adapter assembly 10 is releasably coupled to an actuation assembly 300 in the form of a powered handle. The actuation assembly 300 includes a coupler 310 and actuation controls 320. The actuation controls 320 are operable to selectively activate motors (not explicitly shown) that rotate drive shafts 84a-c (FIG. 15) to actuate functions of an end effector or tool assembly 380 (e.g., drawing an anvil 392 towards a loading unit 390, firing staples from the loading unit 390, extending a knife from the loading unit 390, etc.). For a detailed description of the structure and function of an exemplary powered handle, please refer to U.S. Pat. No. 9,055,943 ("the '943 patent"), the entire contents of which are incorporated herein by reference. It is contemplated that the adapter assembly 10 can be configured for selective connection to a manually actuated actuation assembly such as described in U.S. Pat. No. 8,789,737, the entire contents of which are incorporated herein by reference.

The adapter assembly 10 includes a proximal end portion or base 20 that is releasably received by the coupler 310. An elongate coupling body 70 extends distally from the base 20 and has a distal end 90 configured for releasable connection with an extension assembly 290. The extension assembly 290 has a distal portion configured for releasable connection with the tool assembly 380. In exemplary embodiments, the tool assembly 380 includes a loading unit 390 and an anvil 392 for applying a circular array of staples (not shown) to tissue (not shown).

Alternatively, the elongate coupling body 70 and the extension assembly 290 can be integrally formed. In embodiments, the extension assembly 290, and/or the elongate coupling body 70, includes a shaft 292 that extends from the distal end 90 of the adapter assembly 10 to the tool assembly 380. As shown, the shaft 292 has a first end 292a and a second end 292b and a curved central section between the first and second ends 292a, 292b; however, it is contemplated that the shaft 292 can be substantially linear or have any suitable configuration between the first and second ends 292a, 292b. For a detailed description of an exemplary extension assembly and tool assembly reference can be made to the '943 patent.

Although aspects of the present disclosure will be shown and described as relates to the adapter assembly 10, it is envisioned that the aspects of the present disclosure may be adapted for use with adapter assemblies having an alternative configuration. For a detailed description of exemplary adapter assemblies and exemplary extension assemblies reference can be made to commonly owned U.S. patent application Ser. No. 14/875,766 ("the '766 application"), filed Oct. 6, 2015, the content of which is incorporated by reference herein in its entirety.

Figure 3:
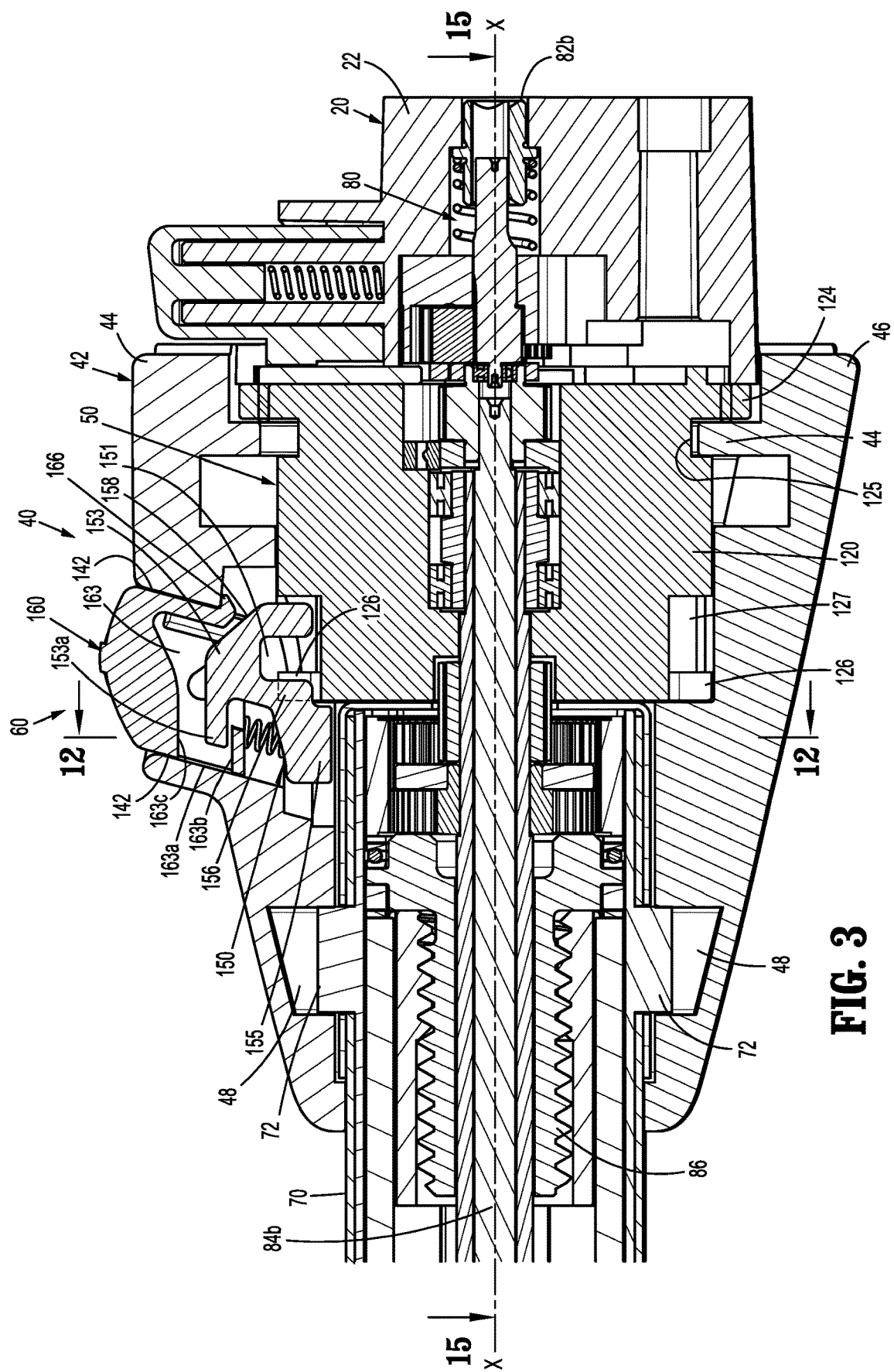
FIG. 3 is a cross-sectional view taken along section line 3-3 of FIG. 2.

With reference to FIGS. 2 and 3, the adapter assembly 10 includes the base 20 and a rotation assembly 40. The base 20 includes a coupling assembly 22 and a base member 50. The base 20 defines a longitudinal axis X-X (FIG. 3) of the adapter assembly 10. The rotation assembly 40 includes a housing 42 that is rotatably supported about the base 20 and an elongate coupling body 70 that extends distally from the housing 42. The adapter assembly 10 also includes a drive assembly 80 (FIG. 3) that extends through the coupling assembly 22, the housing 42, and the elongate coupling body 70 to transfer power from the coupler 310 (FIG. 1) of the actuation assembly 300 to the tool assembly 380 (FIG. 1). The coupling assembly 22 is configured to releasably secure the adapter assembly 10 to the coupler 310 of the actuation assembly 300 (FIG. 1).

Figure 16:
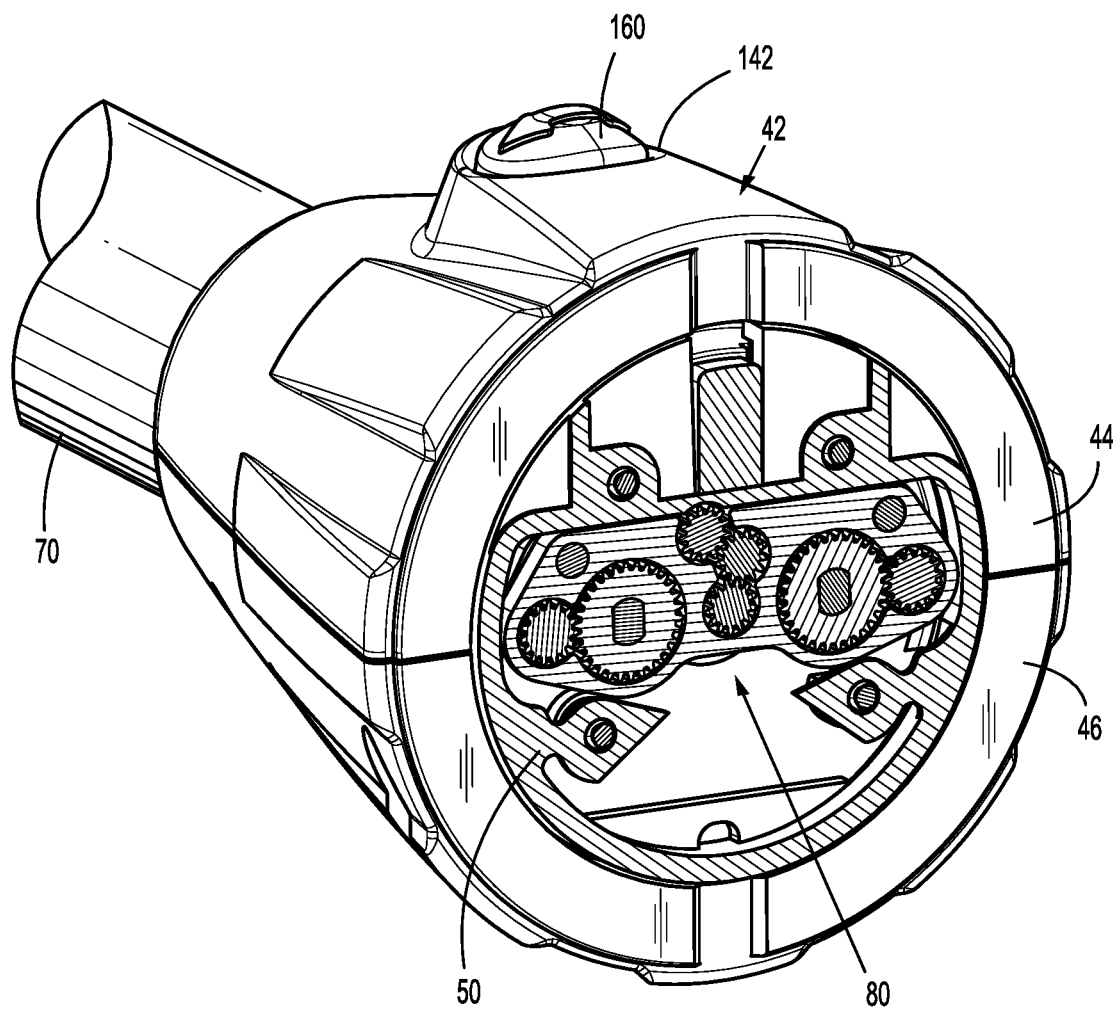
FIG. 16 is a cross-sectional view taken along section line 16-16 of FIG. 15.

Briefly, the drive assembly 80 of the adapter assembly 10 includes first, second, and third connectors 82a, 82b, 82c (FIG. 2) configured for operable connection with first, second, and third drive shafts (not shown) of the actuation assembly 300. As shown in FIG. 3, the second connector 82b is operably connected to an elongate drive shaft 84b of the drive assembly 80 for transferring rotational motion from the actuation assembly 300 through the adapter assembly 10. Each of the first and third connectors 82a, 82c are operably connected to planetary gear assemblies 86 (FIG. 16) supported within the adapter assembly 10. The planetary gear assemblies 86 are configured to convert the rotational motion from the drive shafts of the actuation assembly 300 to longitudinal motion of the drive shafts 84a-c to facilitate operation of the tool assembly 380. For a detailed description of exemplary adapter assemblies, including an exemplary coupling assembly and exemplary drive assemblies, please refer to the '766 application, the content of which was previously incorporated by reference herein.

Figure 4:
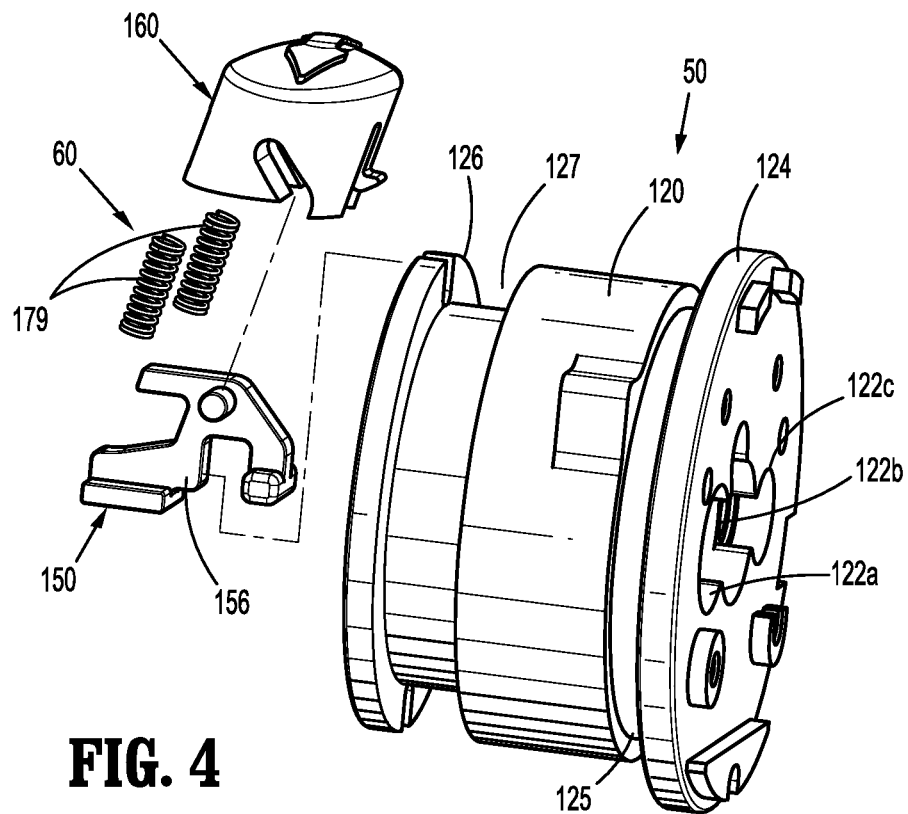
FIG. 4 is a perspective, exploded view of a locking mechanism and a base member of the adapter assembly of FIG. 3.

With reference to FIGS. 2-4, the rotation assembly 40 of the adapter assembly 10 includes the housing 42 that is rotatably supported on the base member 50 and a locking mechanism 60 disposed within the housing 42. The housing 42 supports the elongate coupling body 70. As will be described in further detail below, the locking mechanism 60 has a locked position (FIG. 3) in which the housing 42 is rotationally secured relative to the base member 50 and an unlocked position (FIG. 13) in which the housing 42 is rotatable about the longitudinal axis X-X in relation to the base member 50. As described in further detail below, the tool assembly 380 is rotatably fixed to a distal portion of the extension assembly 290 which is rotatably fixed to the distal portion of the elongate coupling body 70. As such, rotation of the housing 42 about the longitudinal axis X-X of the adapter assembly 10 causes the tool assembly 380 (FIG. 1), which defines a longitudinal axis Y-Y (FIG. 1), to rotate about the longitudinal axis X-X of the adapter assembly 10 to facilitate repositioning of the tool assembly 380 relative to the actuation assembly 300. This enables a clinician to orient the tool assembly 380 relative to the actuation assembly 300 without changing the orientation of the actuation assembly 300.

The housing 42 may be formed from a first body shell 44 and a second body shell 46. Each of the first and second body shells 44, 46 form approximately half of the housing 42 and are joined together by fasteners 47. Alternatively, the first and second body shells 44 and 46 may be secured together by welding or the like. Each of the first and second body shells 44, 46 define a recess 48 (FIG. 3) that extends about the elongate coupling body 70. The elongate coupling body 70 has an outer surface that includes tabs 72 that are received within a respective one of the recesses 48 to rotatably fix the elongate coupling body 70 to the housing 42.

Figure 5:
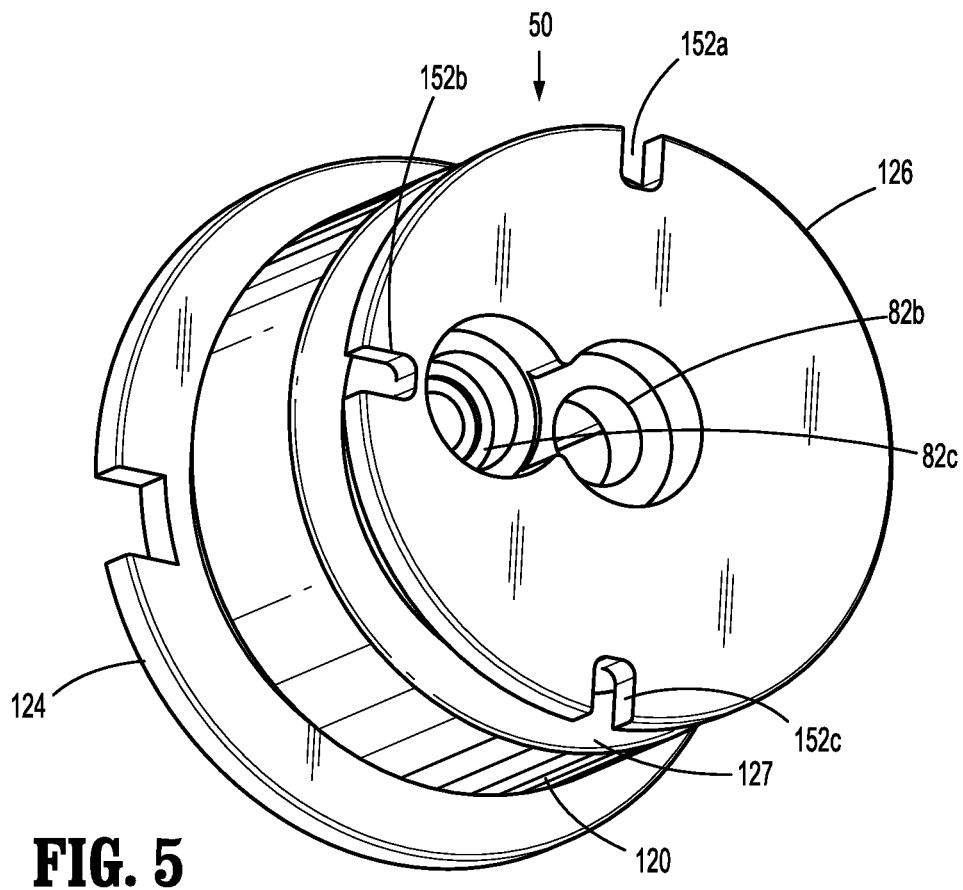
FIG. 5 is a front perspective view of the base member of FIG. 4.

Referring to FIGS. 4 and 5, the base member 50 includes a substantially cylindrical member 120 defining longitudinal openings 122a, 122b, 122c that are configured to receive the drive assembly 80 (FIG. 3). The base member 50 also includes proximal and distal annular flanges 124, 126 and further defines proximal and distal annular grooves 125, 127. The proximal annular flange 124 facilitates attachment of the base member 50 to the coupling assembly 22. The proximal annular groove 125 accommodates an annular retention flange 49 (FIG. 3) of the housing 42 to longitudinally secure the housing 42 relative to the base member 50 while allowing the housing 42 to rotate about the base member 50.

With reference to FIGS. 4-6, the distal annular flange 126 and the distal annular groove 127 of the base member 50 operate in combination with the locking mechanism 60 to secure the housing 42 in fixed rotational orientation relative to the base member 50. In particular, the distal annular flange 126 of the base member 50 defines a plurality of lock cutouts, e.g., first, second, and third lock cutouts 152a-c, that are configured to receive a lock 156 of the locking mechanism 60 as described in greater detail below to retain the housing 42 in one of a plurality of fixed positions in relation to the base member 50. As shown the first and third lock cutouts 152a, 152c are diametrically opposed to one another and the second lock cutout 152b oriented halfway between the first and third lock cutouts 152a, 152c. It is envisioned that the distal annular flange 126 may define any number of lock cutouts which may be arranged in any suitable configuration. For example, the lock cutouts may be arranged in set intervals, uniformly or randomly spaced, and, where the drive assembly 80 permits, the lock cutouts may be formed to extend entirely around the distal annular flange 126 to permit locking of the housing 42 in any three-hundred sixty degree (360°) orientation about the base member 50.

Figure 13:
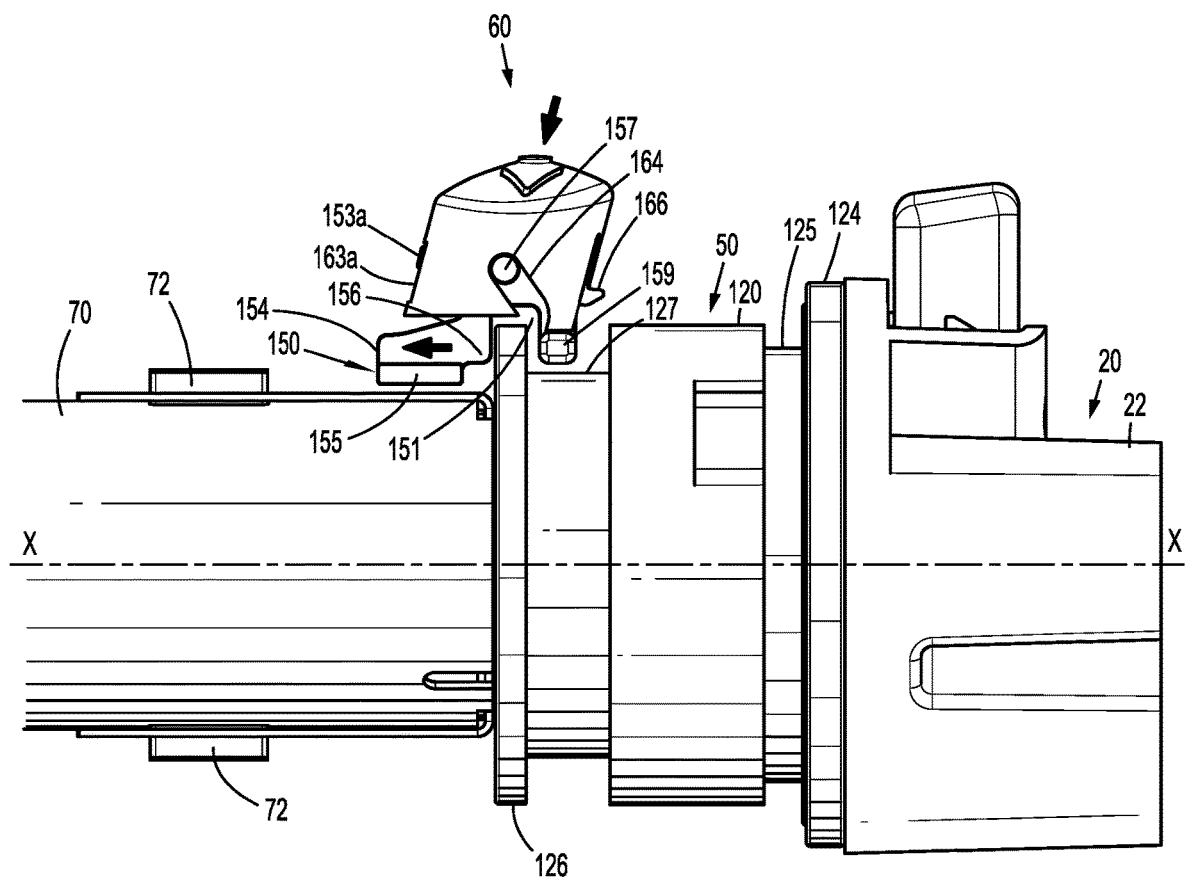
FIG. 13 is a side view of the proximal portion of the adapter assembly with a housing of the adapter assembly removed and the locking mechanism in an unlocked position.

Referring now to FIGS. 4 and 7-10, in embodiments, the locking mechanism 60 includes the locking member 150, a button 160, and biasing members 179. With particular reference to FIGS. 7 and 8, the locking member 150 includes a body 153, a distal leg 154, and a proximal leg 158. The body 153 defines a body axis B-B that passes through the distal and proximal legs 154, 158. The body 153 includes a finger 153*a* that extends over the distal leg 154 and bosses 157 that extend from the body 153 in a direction orthogonal to the body axis B-B. The distal leg 154 includes a stop 155 and a lock 156. The stop 155 forms a T-shape with the distal leg 154 and has a width greater than the width of the lock cutouts 152*a-c* such that the stop 155 prevents the distal leg 154 from passing entirely through the lock cutouts 152*a-c*. The lock 156 is sized and dimensioned to be positioned within a respective one of the lock cutouts 152*a-c* when the locking member 150 is in a locked position to prevent rotation of the housing 42 relative to the base member 50. The lock 156 extends proximally from the distal leg 154 and is configured such that when the lock 156 is positioned in a respective one of the lock cutouts 152*a-c*, the stop 155 abuts the distal annular flange 126. The proximal leg 158 includes a foot 159 that is positioned within the distal annular groove 127 of the base member 50. The distal leg 154 and the proximal leg 158 define a gap 151 therebetween that is sized and dimensioned to allow the distal annular flange 126 to rotate within the gap 151 when the locking member 150 is in an unlocked position as shown in FIG. 13.

Figure 9:
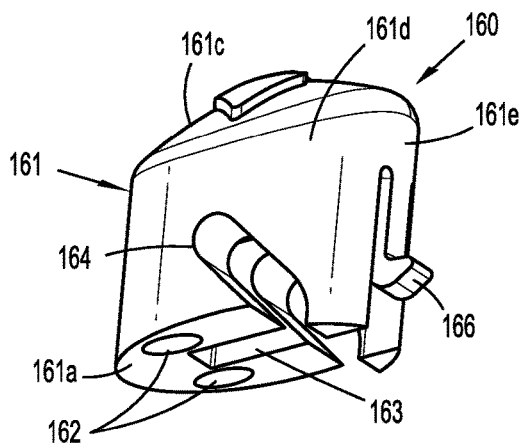
FIG. 9 is a bottom perspective view of a button of the locking mechanism of FIG. 4.
Figure 10:
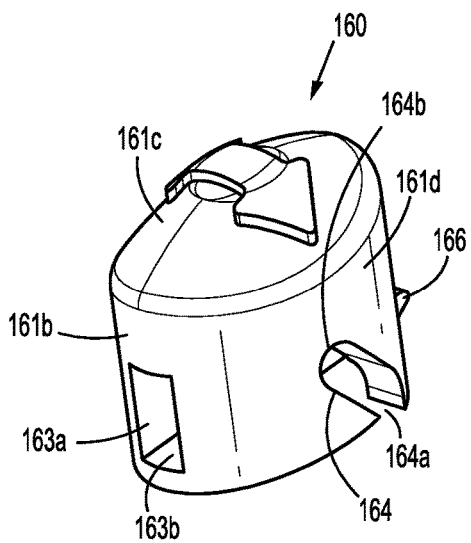
FIG. 10 is a top perspective view of the button of the locking mechanism of FIG. 4.

Referring now to FIGS. 9 and 10, the button 160 has a button body 161 that defines blind holes 162, an opening 163, and camming slots 164. The opening 163 extends inward from a bottom surface 161*a* of the button body 161 to define a distal opening 163*a* in a distal surface 161*b* of the body 161. The distal opening 163*a* includes a shelf 163*b* opposite the bottom surface 161*a* of the button body 161. The blind holes 162 extend substantially vertically from the bottom surface 161*a* of the button body 161 on either side of the opening 163 in a direction orthogonal to a plane defined by the bottom surface 161*a*. The blind holes 162 may be substantially cylindrical and are sized to receive the biasing members 179 (FIG. 4).

The camming slots 164 pass entirely through side surfaces 161*d* of the button body 161. The camming slots 164 extend from a first end 164*a* of the button body 161 adjacent the bottom surface 161*a* of the button body 161 and a proximal surface 161*e* of the button body 161 to a second end 164*b* of the button body 161 adjacent the distal surface 161*b* and a top surface 161*c* of the button body 161 such that the cam slots 164 are inclined distally upward when the button 160 is viewed in profile. The camming slots 164 are in communication with the opening 163 and configured to receive the bosses 157 of the locking member 150 such that vertical movement of the button 160 (i.e., movement substantially towards and away from the longitudinal axis X-X as viewed in FIG. 11) affects longitudinal translation of the locking member 150 as described in detail below.

Figure 11:
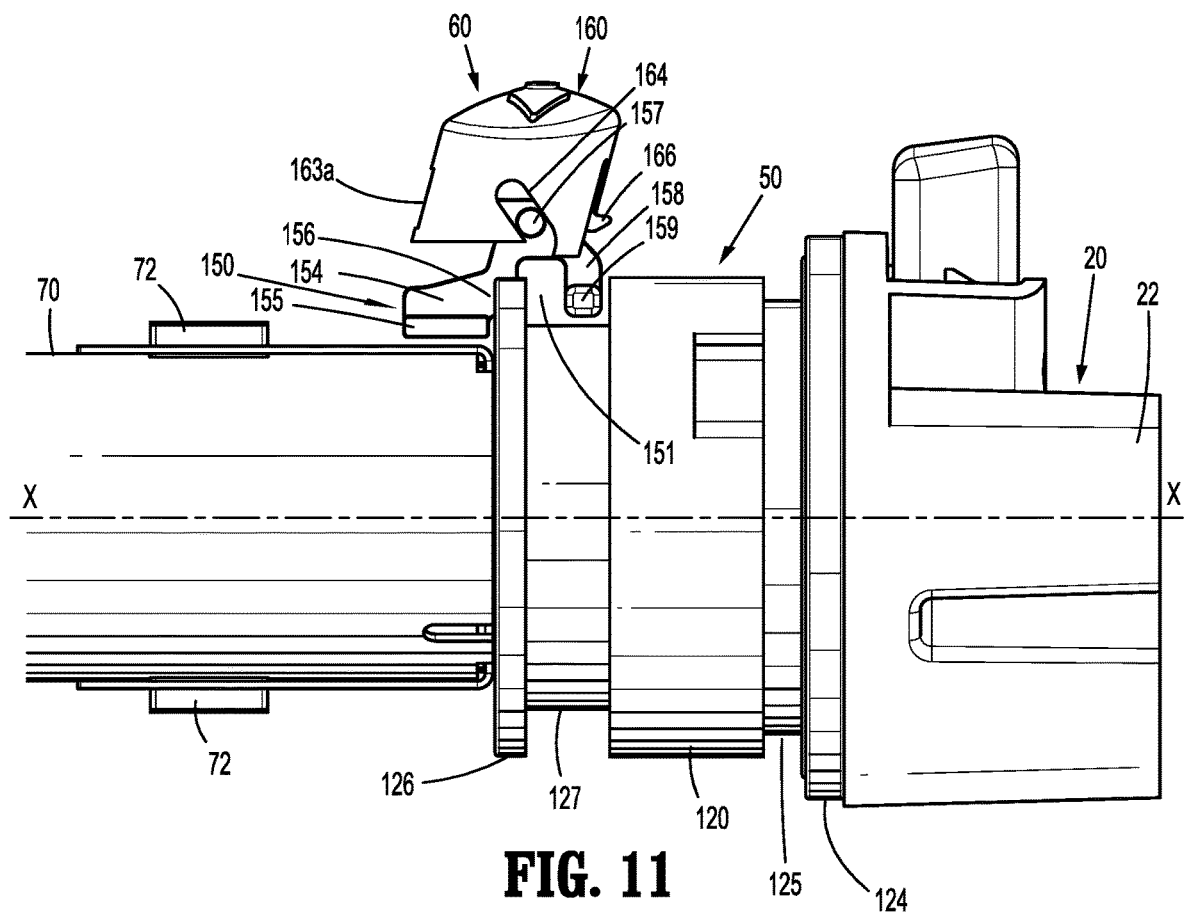
FIG. 11 is a side view of the proximal portion of the adapter assembly shown in FIG. 2 with a housing of the adapter assembly removed and the locking mechanism in a locked position.
Figure 12:
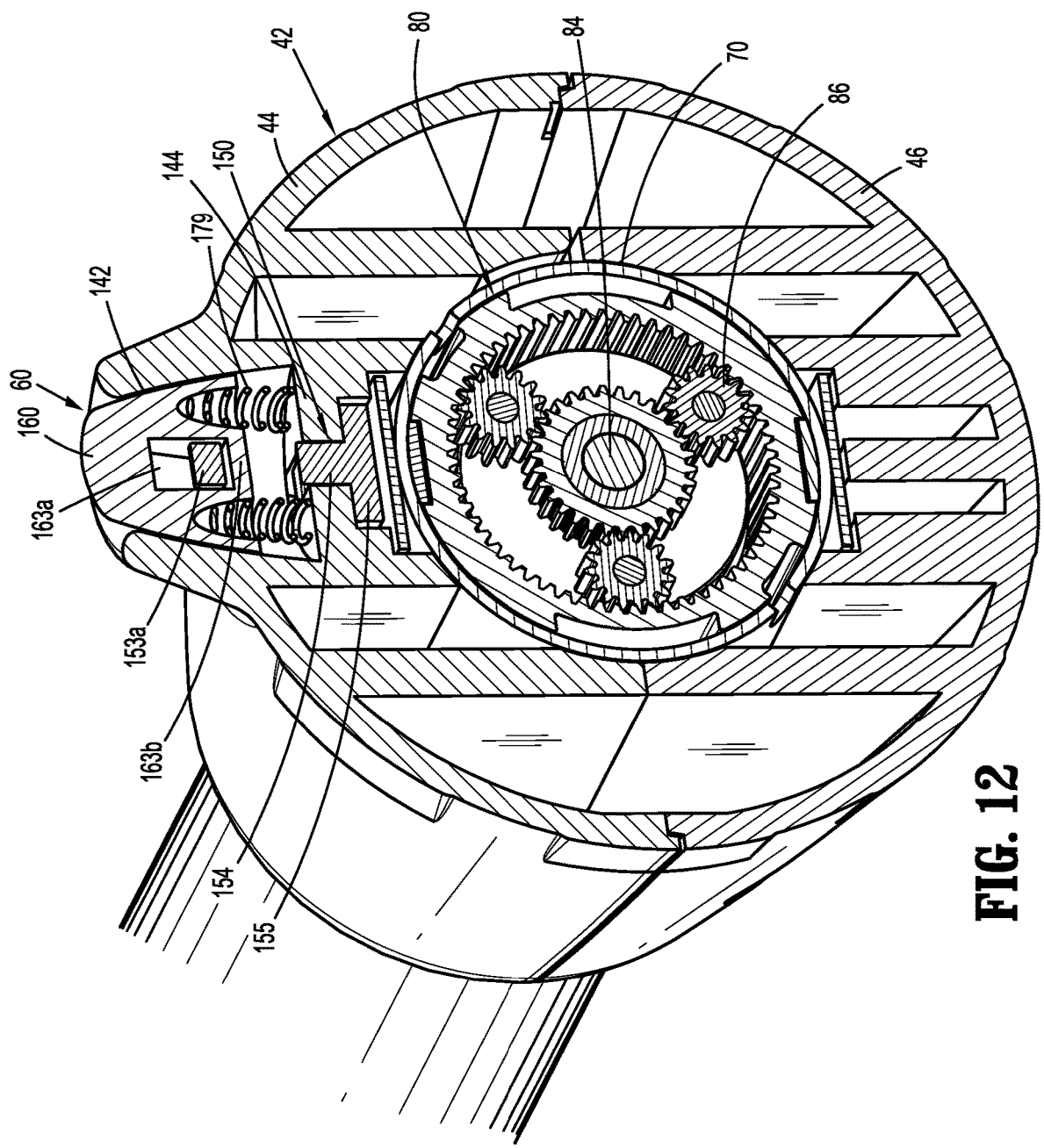
FIG. 12 is a cross-sectional view taken along section line 12-12 of FIG. 3.

Referring to FIGS. 3, 11, and 12, the locking mechanism 60 is disposed in a channel 142 defined in the housing 42. The locking mechanism 60 is positioned on the base member 50 adjacent the distal annular flange 126. In a locked position of the locking mechanism 60, the lock 156 is disposed within one of the lock cutouts 152*a-c* defined in the distal annular flange 126 to rotatably fix the orientation of the housing 42 relative to the base member 50. The button 160 is positioned radially outward of the locking member 150 such that the body 153 of the locking member 150 is disposed within the opening 163 of the button 160. When the body 153 is disposed within the opening 163, the bosses 157 of the locking member 150 are slidingly received within the cam slots 164. In addition, the biasing members 179 are received within the blind holes 162 to urge the button 160 away from the locking member 150. In this position, the locking member 150, due to engagement with the portion of the button 160 defining the cam slots 164, is urged proximally to the locked position.

With particular reference to FIG. 12, the biasing members 179 are supported on a ledge 144 of the body shell 44 to bias the button 160 away from the locking member 150. However, it is contemplated that the biasing members 179 may be supported by and be slidable along a top surface of the stop 155.

Briefly referring back to FIG. 3, the finger 153*a* of the locking member 150 extends distally within the opening 163 of the button 160 such that the finger 153*a* is positioned over the shelf 163*b* of the button 160 to retain the button 160 within the channel 142 of the housing 42. In addition, the proximal surface 161*e* (FIG. 9) of the button 160 can include a retention hook 166 that extends proximally from the proximal surface 161*e* of the button 160 into engagement with the housing 42 to retain the button 160 within the channel 142.

Figure 14:
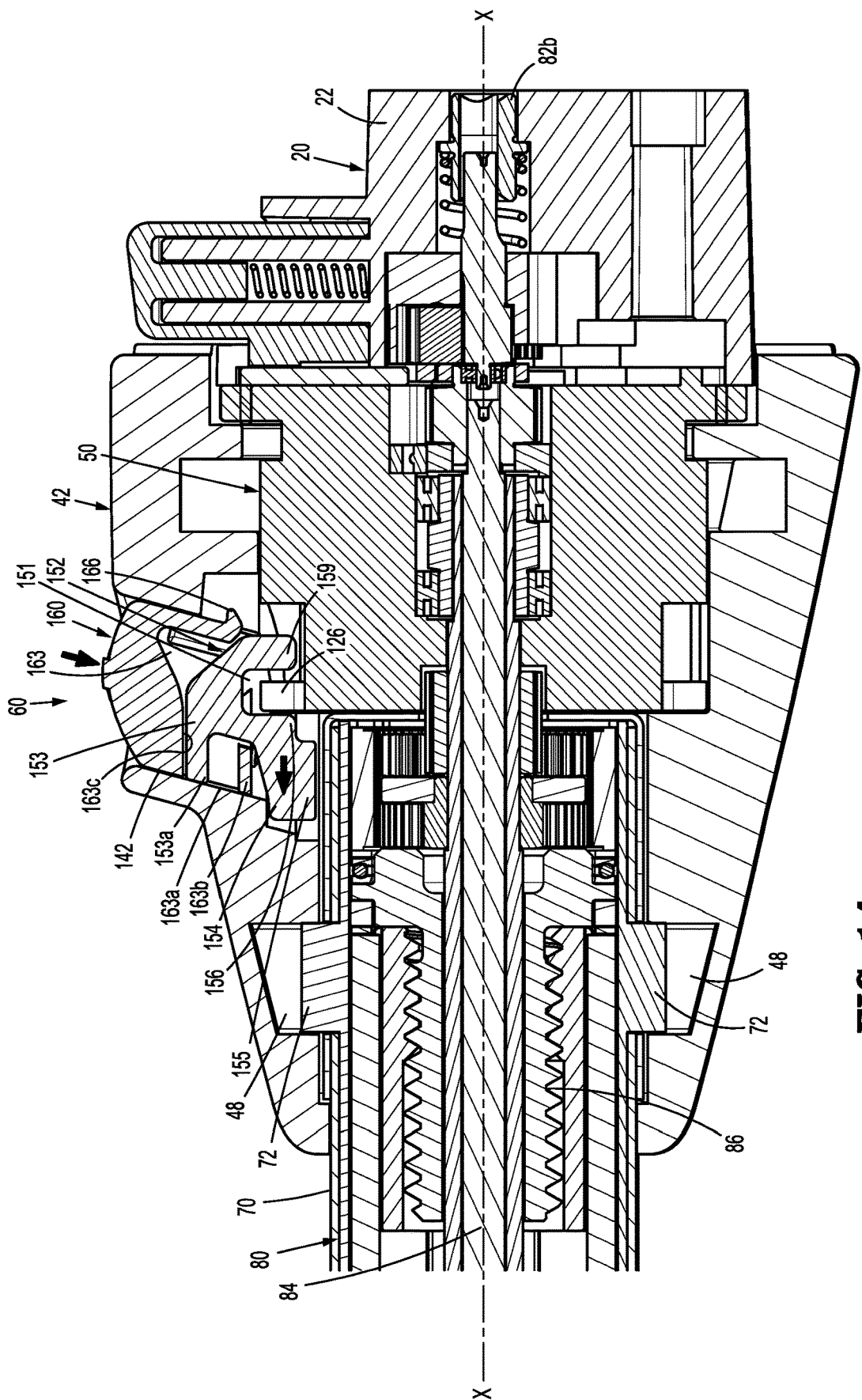
FIG. 14 is a side cross-sectional view of the proximal portion of the adapter assembly of FIG. 13.

Referring to FIG. 11, in the unlocked position of the locking mechanism 60, the button 160 is urged upwardly by the biasing members 179 such that the locking member 150 is cammed by the bosses 157 to a proximal position. In the proximal position, the lock 156 is positioned within a lock cutout 152*a-c* of the flange 126 of the base member 50 to prevent rotation of the housing 42 in relation to the base member 50. Referring now to FIGS. 13 and 14, to move the lock mechanism 60 to the unlocked position, the button 160 is depressed within the channel 142 of the housing 42 against the bias members 179. As the button 160 is depressed, the button 160 is confined to substantially vertical movement (movement towards and away from the longitudinal axis X-X) within the channel 142 of the housing 42. As the button 160 is depressed, the bosses 157 slide within the cam slots 164 to affect distal longitudinal movement of the locking member 150 relative to the housing 42. Specifically, walls defining the cam slots 164 engage the bosses 157 to translate the locking member 150 in a direction substantially parallel to the longitudinal axis X-X. As the locking member 150 moves distally relative to the button 160, the lock 156 moves from within a cutout 152*a-c* to a position distal of the distal annular flange 126, and thus out of the lock cutout 152*a-c*. In this position, the housing 42 is free to rotate about the base member 50. As the locking member 150 moves distally, the foot 159 of the proximal leg 158 slides within the distal annular groove 127 and may abut the distal annular flange 126 to limit distal movement of the locking member 150. In embodiments, contact between the foot 159 of the locking member 150 with the distal annular flange 126 may provide tactile feedback to a clinician that the button 160 is fully depressed and/or that the locking mechanism 60 is in the unlocked position. In addition, when the button 160 is fully depressed, the body 153 of the locking member 150 may engage a roof 163*c* of the opening 163 to limit depression of the button 160 and/or distal movement of the locking member 150.

With reference to FIGS. 15-18, with the locking mechanism 60 in the unlocked position, the housing 42 is rotatable about the base member 50, the coupling assembly 22, and the drive assembly 80. Rotation of the housing 42 also rotates the elongate coupling body 70 about the longitudinal axis X-X through the engagement of the tabs 72 (FIG. 14) with the housing 42.

With particular reference to FIGS. 17 and 18, when the housing 42 is rotated from a first radial position (FIG. 17) to a second radial position (FIG. 18), the extension assembly 290 is rotated with the distal end 90 of the elongate coupling body 70. The extension assembly 290 has a tool coupler 294 on a distal portion thereof that releasably secures the tool assembly 380 (FIG. 1) to the extension assembly 290. As shown, rotation of the housing 42 about the longitudinal axis X-X of the adapter assembly 10 changes the position of the tool coupler 294, and thus, the position of a tool assembly 380 secured to the tool coupler 294, relative to the coupling assembly 22. As the housing 42 is rotated, the drive assembly 80 maintains its position relative to the coupling assembly 22. It will be appreciated that when the coupling assembly 22 is secured to the actuation assembly 300 (FIG. 1), rotation of the housing 42 in relation to the actuation assembly 300 allows a clinician to reposition the tool assembly 380 (FIG. 1) without having to reposition the actuation assembly 300.

If the housing 42 is rotated relative to the base member 50 with the lock cutouts 152a-c misaligned with the lock 156 and the button 160 is released, the lock 156 will abut the distal annular flange 126 until the lock 156 is aligned with one of the lock cutouts 152a-c. When the lock 156 is aligned with one of the lock cutouts 152a-c, the biasing members 179 will urge the button 160 away from the longitudinal axis X-X and affect proximal movement of the locking member 150 such that the lock 156 will slide into the aligned lock cutout 152a-c. When the lock 156 slides into the aligned lock cutout 152a-c, the slider 155 may contact the distal annular flange 126 to provide audible indicia (a "click") that the housing 42 is rotationally secured to the base member 50.

While rotation of the housing 42 about the base member 50 is detailed above, it is contemplated that the base member 50 may be rotated within the housing 42 such that the actuation assembly 300 is repositionable relative to the tool assembly 380 while tool assembly 380 remains substantially stationary within a surgical site.

The rotation assembly can be incorporated into surgical instrument such as ultrasonic cutting instruments, surgical staplers, surgical clip appliers, and the like. In one example, the surgical instrument has a circular anvil and circular staple cartridge for applying circular rows of staples, as is known. Linear endoscopic staplers are another example. The rotation assembly can be incorporated into an elongate shaft of a manually operated or motorized surgical instrument. The elongate shaft can be integral with the handle or can be provided as an adapter that attaches to a handle, and also attaches to a loading unit. Furthermore, the rotation assembly can be incorporated into a device for use with a robotic surgical system.

Any of the components described herein may be fabricated from either metals, plastics, resins, composites or the like taking into consideration strength, durability, wearability, weight, resistance to corrosion, ease of manufacturing, cost of manufacturing, and the like.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. The present disclosure is not limited to circular stapling loading units, but has application to loading units for linear stapling or other types of instruments, such as electrocautery or ultrasonic instruments. Therefore, the above description should not be construed as limiting, but merely as exemplifications of particular embodiments. Those skilled in the art will envision other modifications within the scope of the claims appended hereto.

What is claimed is:

1. A surgical device comprising:
   a handle;
   a tool assembly; and
   an adapter assembly interconnecting the handle and the tool assembly, the adapter assembly including:
   a base member defining a longitudinal axis;
   a housing rotatably secured to the base member, the housing rotatable in relation to the base member between a plurality of positions, rotation of the housing affecting a position of the tool assembly relative to the handle; and
   a locking mechanism supported on the housing, the locking mechanism including:
   a locking member moveable from a locked position in which a lock of the locking member is engaged with the base member to secure the housing in one of the plurality of positions to an unlocked position in which the housing is rotatable in relation to the base member; and
   a button positioned on the base member and depressible to translate the locking member in a direction parallel to the longitudinal axis of the base member from the locked position to the unlocked position.

2. The surgical device according to claim 1, further comprising an extension assembly including a shaft having a first end and a second end, the first end of the shaft releasably coupled to a distal end of the adapter assembly and the second end of the shaft supporting the tool assembly.

3. The surgical device according to claim 2, wherein the shaft is curved between the first and second ends.

4. The surgical device according to claim 1, wherein the adapter assembly includes a coupling body extending from the base member, the coupling body rotatably fixed to the housing.

5. The surgical device according to claim 1, wherein the adapter assembly includes a coupling assembly extending proximally from the base member and releasably secured to the handle.

6. The surgical device according to claim 5, wherein the adapter assembly includes a drive assembly that extends through the coupling assembly, the base member, and the housing, and wherein the handle engages the drive assembly to actuate the tool assembly.

7. The surgical device according to claim 6, wherein the drive assembly includes a first connector and a second connector disposed within the coupling assembly, the first connector offset from the longitudinal axis.

* * * * *